(12) United States Patent
Wong

(10) Patent No.: US 8,148,691 B1
(45) Date of Patent: Apr. 3, 2012

(54) CALIBRATION METHODOLOGY FOR NDIR DEW POINT SENSORS

(76) Inventor: Jacob Y Wong, Goleta, CA (US)

( * ) Notice: Subject to any disclaimer, the term of this patent is extended or adjusted under 35 U.S.C. 154(b) by 0 days.

(21) Appl. No.: 13/192,863

(22) Filed: Jul. 28, 2011

Related U.S. Application Data

(63) Continuation-in-part of application No. 12/859,749, filed on Aug. 19, 2010.

(60) Provisional application No. 61/274,874, filed on Aug. 21, 2009.

(51) Int. Cl.
*G01J 5/02* (2006.01)

(52) U.S. Cl. ........... 250/340; 250/338.1; 250/339.06; 250/339.12; 250/339.13; 250/252.1; 73/1.03; 73/1.06

(58) Field of Classification Search ............ 250/338.1, 250/339.06, 339.12, 339.13, 340, 252.1; 73/1.03, 1.06
See application file for complete search history.

(56) References Cited

U.S. PATENT DOCUMENTS

| | | | | |
|---|---|---|---|---|
| 5,369,397 A | * | 11/1994 | Wong | 340/632 |
| 5,747,809 A | * | 5/1998 | Eckstrom | 250/345 |
| 5,850,354 A | * | 12/1998 | Bramley et al. | 702/85 |
| 6,202,032 B1 | * | 3/2001 | Hirai et al. | 702/100 |
| 6,469,303 B1 | * | 10/2002 | Sun et al. | 250/343 |
| 7,026,165 B2 | * | 4/2006 | DeGrandpre | 436/164 |
| 7,071,470 B2 | * | 7/2006 | Nomura et al. | 250/339.13 |
| 2006/0084180 A1 | * | 4/2006 | Paldus et al. | 436/171 |
| 2008/0185524 A1 | * | 8/2008 | Kanstad | 250/338.5 |

* cited by examiner

*Primary Examiner* — David Porta
*Assistant Examiner* — Djura Malevic
(74) *Attorney, Agent, or Firm* — Wagner, Anderson & Bright, P.C.

(57) ABSTRACT

A method for calibrating a dual-beam NDIR gas sensor for detecting water vapor by obtaining a variant sensor components domain ("$G_0$") when there is no water vapor gas in the sample chamber, obtaining a physics measurement domain ("G") for a set of known concentrations of the water vapor gas in the sample chamber, the known concentrations being measurable quantities exceeding zero, using G to calculate a $G_{0i}$ from a known concentration of water vapor in the sample chamber for each of multiple master calibration curves, and then selecting the master calibration curve with the lowest difference between its $G_{0i}$ and the $G_0$ of the NDIR gas sensor as the calibration curve. G and the $G_{0i}$ are obtained, preferably, at substantially the same temperature, G is a signal channel output ("$V_S$") divided by a reference channel output ("$V_R$"), and the master calibration curves are obtained from a set of multiple calibration curves obtained from a large number of NDIR gas sensors, each of the calibration curves being represented by an equation of $P=F(G/G_0)$ where P is equal to a gas pressure and F is a function.

12 Claims, 3 Drawing Sheets

CALIBRATION METHODOLOGY FOR NDIR DEW POINT SENSORS

CROSS-REFERENCE TO RELATED APPLICATIONS

This application claims priority from and is a continuation-in-part application of U.S. Ser. No. 12/859,749, filed Aug. 19, 2010 which claims priority from U.S. 61/274,874, filed Aug. 21, 2009.

FIELD OF THE INVENTION

The present invention is in the field of measuring instruments, and specifically relates to a method for calibrating non-dispersive infrared (NDIR) dew point sensors.

BACKGROUND OF THE INVENTION

Moisture is an important issue in many air systems, including ambient air. Its content in controlled air systems must be carefully measured and controlled through use of dew point sensors. The use of dew point temperature of a volume of air (expressed in ° F. or ° C.) to indicate the amount of moisture in it is based upon the operational principle of cooling a volume of air and monitoring the temperature of a surface when condensation first forms on it. The three most common types of sensors for measuring dew point today are chilled mirrors, metal oxide and polymer sensors.

Of the three most common types of dew point sensors, chilled mirror technology can offer the highest accuracy over a wide range of dew points. The operational principle is based on the fundamental definition of dew point—cooling a volume of air until condensation forms. A gas sample passes over a metallic mirror surface which is chilled by a cooler. Light is then directed at the mirror allowing an optical sensor to measure the amount of reflected light. When the mirror is cooled to the point at which condensation begins to form on its surface (i.e. the dew point has been reached), the amount of light reflected by the mirror diminishes which is in turn detected by an optical sensor. The rate of cooling is then carefully regulated by a temperature sensor on the mirror. Once a state of equilibrium has been reached between the rate of evaporation and condensation, the mirror temperature is equal to the dew point. Although chilled mirror technology offers the highest accuracy in dew point measurements, a dew point sensor designed around it is in essence a very delicate and precision optical instrument. Its optical measurement principle is highly sensitive to the presence of dirt, oil, dust and other contaminants on the mirror surface. In addition, to correctly calibrate such a precision optical instrument requires not only expertly trained know-how in this technology field with years of experience but also a lot of time and effort required to be spent in doing it. It is therefore not surprising that chilled mirror dew point sensors are extremely expensive and are only employed when absolute accuracy is essential. Furthermore, frequent maintenance, cleaning and calibration must also be regularly performed on them in order for them to function properly.

Capacitive metal oxide sensors, including aluminum oxide technology, are designed for very low dew point measurement in industrial processes. While the types of materials used in construction can vary, the sensor structure and operating principle generally remain the same. Capacitive sensors are built in a layered structure sandwiching together a substrate base layer, a lower electrode, a hygroscopic metal-oxide middle layer, and a water permeable upper electrode. The capacitance across the upper and lower electrode changes based on the amount of water vapor absorbed by the metal oxide layer (the dielectric of the capacitor), which is a function of dew point. While capacitive sensors provide excellent low dew point measurement accuracy to −100° C. and lower, they tend to offer poor long-term stability in processes with varying dew points at the higher ranges (e.g. refrigerant dried systems). Metal oxide sensors can also be easily damaged by high humidity levels and condensation. Drift in the output reading means frequent calibration which requires rather sophisticated and complex instrumentation that can only be done at the manufacturer's calibration laboratories.

Capacitive polymer sensors measure accurately over a wider humidity range than metal oxide counterparts and, although still not totally satisfactory, also offer better long-term stability than capacitive metal oxide sensors. While the capacitive operating principle is similar to that of metal oxide, there are a few key differences. Beyond the obvious material difference in the hygroscopic layer (polymer vs. metal oxide), a capacitive polymer sensor is also bonded together with a resistive temperature sensor. The polymer sensor measures the humidity (amount of water molecules in the measured gas) in terms of relative humidity (RH) while the temperature sensor measures the temperature of the polymer sensor. From these two values, the microprocessor in the transmitter electronics calculates the dew point temperature. Like the capacitive metal oxide sensors, calibration of capacitive polymer sensors also requires sophisticated and complex instrumentation and can only be performed at the manufacturer's laboratories prior to shipping to distributors or end-users.

It can be seen from the foregoing discussion that just about all dew point sensors available for sale today require rather elaborate and time-consuming calibration procedures at the factory prior to shipment to customers. With the exception of chilled mirror sensors, the metal oxide and polymer sensors typically have a rod-like shaped cylindrical probe as part of the sensor. In order to overcome the inconvenience of having to ship these sensors back to the factory for re-calibration if needed, portable high-precision humidity calibrators are available for calibrating metal oxide and polymer sensor probes in the field. The most common one widely used in the field is the two-pressure reactor which is similar in design to precision humidity calibration instruments used in national bureaus for standards. Air or nitrogen at a pressure $P_1$ is led through a chamber partially filled with water and saturated to 100% relative humidity (RH) at $P_1$. By means of a reduction valve, the saturated air is reduced to ambient pressure $P_a$ and fed into a measurement chamber. By design the saturation chamber and the measurement chamber are accurately maintained at the same temperature of $T_a$. Under these conditions, the water-vapor partial pressure $P_w$ is reduced from the saturated vapor pressure $P_{sw}$ at the same ratio as the total pressure or $$P_w = P_{sw} \times (P_a/P_1)$$

From this it follows that:

$$RH = P_w/P_{sw} = P_a/P_1$$

at temperature $T_a$. Thus, the generated relative humidity essentially depends on the ratio of the two pressures.

Despite the fact that a two-pressure reactor can be used to adequately calibrate metal oxide and polymer dew point sensors away from their factories, this instrument is very expensive, typically running between US$20,000.00 to US$30,000.00. Furthermore, experienced technicians are required to operate such an instrument and the time it takes to calibrate a metal oxide or polymer dew point sensor easily runs into two or more hours per probe.

Non-dispersive infrared (NDIR) gas sensors have been considered as one of the best methods for gas measurement since the 1950s. This method takes advantage of the fact that all gases vibrate at a unique frequency based upon their individual molecular makeup. The unique vibration of each type of gas molecule will absorb radiation at very specific and unique wavelengths in the infrared portion of the electromagnetic spectrum. The three most important gases in our atmosphere are Oxygen ($O_2$), Water Vapor ($H_2O$) and Carbon Dioxide ($CO_2$). Since Oxygen has a symmetrical molecular structure, it has no infrared absorption bands available for use with the NDIR gas sensing methodology. Hence NDIR Oxygen sensors simply do not exist. On the other hand, NDIR $CO_2$ sensors today can readily be found almost everywhere. But the most surprising fact is that NDIR $H_2O$ sensors or NDIR dew point sensors, irrespective of their cost, can hardly be found anywhere at all. Obviously their absence is not because water vapor is not an important gas in our atmosphere. Nor it is because of its improper molecular makeup. As a matter of fact, like $CO_2$, $H_2O$ has several very strong and specific infrared absorption bands ideally suitable for use with NDIR gas sensing methodology, the most notable of which is at 2.73µ. So the logical question to ask at this point is why?

As it turns out, water vapor or $H_2O$ is by its nature a very unique and peculiar gas all because of the fact that it has a liquid phase, namely water, between the temperatures of zero (0° C.) and 100° C. No other gas in the atmosphere that we know today has liquid phases in this temperature range. Because of this unique occurrence, the presence or absence of $H_2O$ in an air volume strictly depends upon the latter's temperature relative to its surroundings. If the temperature of the air volume wherein $H_2O$ molecules find themselves in is higher than a physical surface nearby, $H_2O$ molecules will disappear from the air volume by condensing themselves onto the colder surface. If $H_2O$ molecules physically bound to a physical surface whose temperature is higher than that of the air volume surrounding it, the $H_2O$ molecules will disappear from the surface by evaporating themselves into the surrounding air volume. By the same token, how much $H_2O$ one finds above a water surface strictly depends upon the latter's temperature. Because of this unique behavior, $H_2O$ has a nickname and it is called a "Houdini gas". This Houdini act of $H_2O$ would not have been so prominent if not for the fact that such an act can take place in the smallest of volume or surface areas approaching those of molecular sizes. Thus $H_2O$ can disappear to or appear from unimaginably small cracks, crevices or openings. It is in this so-called Houdini behavior of $H_2O$ that we are finally able to find the answer to the earlier question as to why NDIR dew point sensors can rarely or hardly be found anywhere at all.

Earlier it was mentioned that $H_2O$ has a very strong and specific absorption band at 2.73µ in the infrared spectrum. Similar to the case for $CO_2$ gas, this absorption band of $H_2O$ can readily be used to design a simple, reliable and low cost NDIR $H_2O$ or dew point sensor. However, because of the fact that $H_2O$ is a Houdini gas and, unlike $CO_2$, devising an accurate and dependable calibration procedure for NDIR $H_2O$ or dew point sensors is a very serious and expensive proposition. When calibrating an NDIR gas sensor, it is paramount that several gas standards spanning a desirable gas concentration range for the sensor are readily available. For example, if one wishes to calibrate an NDIR $CO_2$ sensor having a measurement range from 0 to 5,000 ppm, one would need at least 6 or 7 gas standards in order to get the job done. These gas standards would probably have concentrations ranging from 0 to 5,000 ppm in increment steps of 1,000 ppm and they should be readily available. This is indeed the case for calibrating an NDIR $CO_2$ sensor. However, for an NDIR $H_2O$ or dew point sensor, because $H_2O$ is a Houdini gas, preparing $H_2O$ gas standards needed for an accurate calibration procedure is not a simple task at all. This does not mean that adequate $H_2O$ gas standards cannot be properly prepared for the task at hand, it is only that the cost and efforts involved in such an undertaking are so prohibitively high as to render these sensors economically vastly disadvantageous when compared with metal oxide or polymer dew point sensors. This is precisely the reason why NDIR $H_2O$ or dew point sensors can rarely be found anywhere.

It is amply clear from the foregoing discussion that low cost NDIR dew point sensors if available for sale today to the public would fill a big vacuum left open by existing available dew point sensors in terms of sensor cost, performance, reliability, long term stability and life. It is the object of the current invention to advance a novel methodology for calibrating NDIR dew point sensors without the need to use the difficult-to-prepare $H_2O$ standards. By so doing, the prohibitively high calibration cost for NDIR dew point sensors will be eliminated thereby opening the door for the possibility of producing such low cost NDIR dew point sensors in the future.

SUMMARY OF THE INVENTION

The present invention is generally directed to a method for calibrating a dual-beam NDIR gas sensor for detecting water vapor by obtaining a variant sensor components domain ("$G_0$") when there is no water vapor gas in the sample chamber, obtaining a physics measurement domain ("G") for a set of known concentrations of the water vapor gas in the sample chamber, the known concentrations being measurable quantities exceeding zero, using G to calculate a $G_{0i}$ from a known concentration of water vapor in the sample chamber for each of multiple master calibration curves, and then selecting the master calibration curve with the lowest difference between its $G_{0i}$ and the $G_0$ of the NDIR gas sensor as the calibration curve.

In other aspects of the present invention, G and the $G_{0i}$ are obtained at substantially the same temperature, G is a signal channel output ("$V_S$") divided by a reference channel output ("$V_R$"), and the master calibration curves are obtained from a set of multiple calibration curves obtained from a large number of NDIR gas sensors, each of the calibration curves being represented by an equation of $P=F(G/G_0)$ where P is equal to a gas pressure and F is a function. The group of master calibration curves can be equally spaced (and have an odd number of curves—e.g., five curves obtained from at least fifty NDIR gas sensors) and represent the range of calibration curves.

In another aspect of the present invention, it is especially preferred that the NDIR gas sensor being calibrated have an infrared source, reference and signal detectors having an identical narrow band pass filter with the same Center Wavelength ("CWL"), Full Width Half Maximum (FWHM) and transmittance efficiency at the CWL for producing reference and signal outputs, a sample chamber having a signal channel path length greater than the reference channel path length, and electronics for determining a sample concentration of water vapor.

Accordingly, it is a primary object of this invention to provide NDIR gas sensors useful for detecting water vapor that can easily be calibrated.

This and further objects and advantages will be apparent to those skilled in the art in connection with the drawings and the detailed description of the invention set forth below.

DETAILED DESCRIPTION OF THE INVENTION

Figure 1:
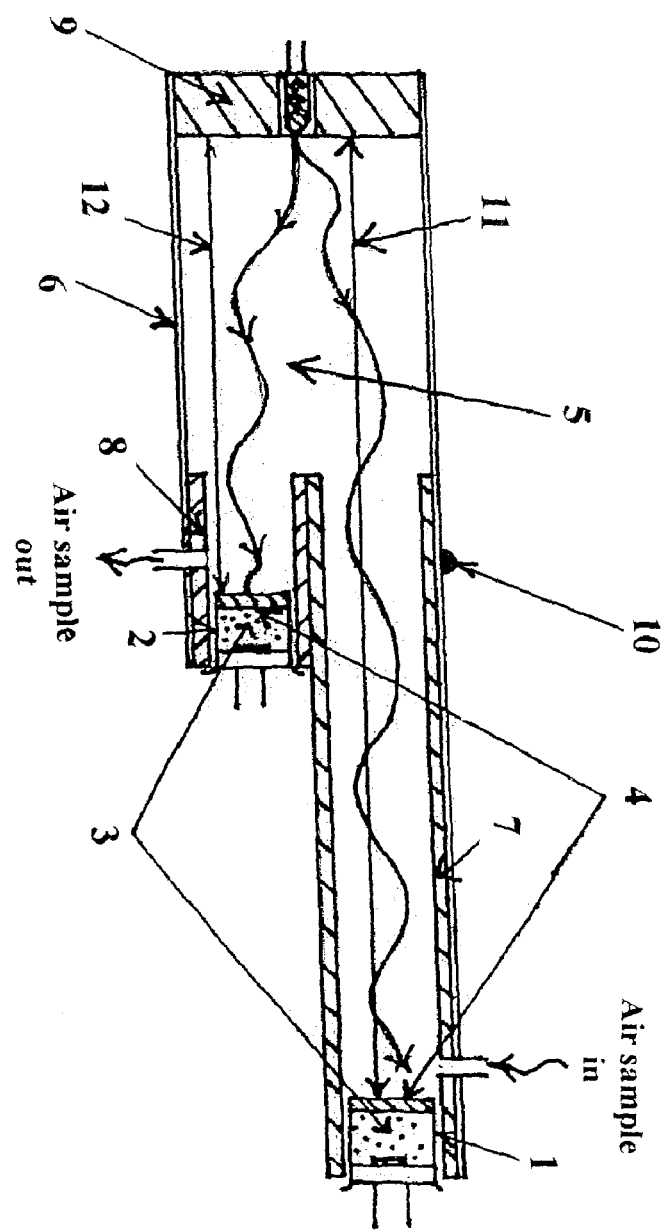
FIG. 1 illustrates one optical component layout for a near zero drift Absorption Biased NDIR $H_2O$ or dew point sensor.

The present invention complements the teaching of advancing a methodology for NDIR gas sensors capable of significantly reducing output drifts over time disclosed in U.S. Ser. No. 12/859,749, the disclosure of which is specifically incorporated herein by reference. It is important to point out the fact that such a methodology only applies to NDIR gas sensors and not to other technology types of gas sensors. It is therefore appropriate to begin the detailed description of the current invention by referencing the inventor's earlier disclosed teaching in the design of a dual-beam NDIR gas sensor that is capable of significantly reducing output drifts over time. Specifically and for purposes of illustration, the dual-beam methodology discussed herein is for the implementation of an NDIR $H_2O$ or dew point gas sensor.

Prior to the teaching disclosed in U.S. Ser. No. 12/859,749, conventional dual-beam methodology utilized a spectral filter for the Signal channel that had its center wavelength (CWL) coincident with that of the gas to be detected. For the case of an NDIR $H_2O$ or dew point sensor, the CWL of the spectral filter would be designed to be at 2.73µ, where there is a strong and specific $H_2O$ absorption band. The CWL of the spectral filter for the Reference channel would be designed at 2.20µ where no absorption bands exist for common gases present in the atmosphere, including $H_2O$. However, as the temperature of the infrared source changes, thereby shifting the Planck's spectral radiation excitance curve, the relative magnitudes of radiation traversing the Signal channel and the Reference channel filters will change. The ratio of their respective detector outputs will therefore also change. This is precisely the reason why the outputs of all NDIR gas sensors utilizing the conventional dual-beam methodology will drift over time as their infrared source ages.

The inventor's earlier teaching disclosed in U.S. Ser. No. 12/859,749 uses the same spectral narrow band pass filter with its CWL coincident with that of the gas to be detected (for $H_2O$, CWL=2.73µ) for both the Signal and the Reference channels. An absorption bias is additionally applied to the Signal channel by making the sample chamber path length associated with it longer than that associated with the Reference channel. By so doing, the ratio of the Signal detector output over the Reference detector output remains almost completely invariant as the infrared source ages thereby significantly reducing sensor output drift over time.

The current invention extends the inventor's earlier modified NDIR dual-beam methodology utilizing identical spectral filters for the Signal and Reference channels and an absorption biased configuration of sensor components as disclosed in U.S. Ser. No. 12/859,749 to include a novel signal processing scheme. This scheme separates the calibration curve for the sensor into two distinct domains. The first domain reflects the Physics of NDIR gas measurement for the sensor and is time invariant. The second domain reflects the characteristics of the sensor components collectively represented by a single parameter which is time variant. Both domains are dependent on the ambient temperature wherein the sensor is located. All the sensor components belonging to the second domain are designed to share the same thermal platform whose temperature, $B_T$, is directly linked to the ambient temperature. $B_T$ is constantly being monitored by the sensor and made known to its processing electronics in order to correct for the overall sensor output as a function of ambient temperature.

The current invention of novel calibration methodology for NDIR $H_2O$ or dew point sensors without the need to use difficult-to-prepare $H_2O$ gas standards is illustrated and explained more fully via the use of FIG. 1. FIG. 1 shows the optical component layout for a near zero drift Absorption Biased NDIR $H_2O$ or dew point sensor. As shown in FIG. 1, both the Signal channel detector 1 and the Reference channel detector 2 are entrapped with 100% nitrogen 3 and have the same narrow band pass spectral filter 4 which is used to detect $H_2O$ present in the sample chamber 5. The filter to be used for the detection of $H_2O$ gas has a CWL=2.57µ and a FWHM=0.16µ. Notice that both detectors 1 and 2 are thermally connected to the entire sensor body 6 through their respective waveguides 7 and 8 and consequently they always share the same thermal platform with each other. In other words, in an especially preferred embodiment, the entire sensor body 6, which is in essence a composite of aluminum parts comprising the infrared source mount 9, sample chamber 5 and the waveguides 7 and 8, respectively, for the Signal and Reference channels, provides an excellent common thermal platform for detectors 1 and 2. (It bears note that such parts might also be made of non-aluminum materials, such as plastic, provided that any alternative material(s) satisfies the functional requirements placed upon it for an NDIR gas sensor, including the ability to successfully and quickly transmit heat so as to create a common thermal platform.) The temperature of this common thermal platform, $B_T$, which is directly linked to the ambient temperature wherein the sensor is located, is monitored constantly via thermistor 10 with its value made known to the processing electronics of the sensor.

The NDIR $H_2O$ or dew point sensor as portrayed in FIG. 1 can be used to determine not only the presence or absence of $H_2O$ in sample chamber 5 but it can also be calibrated to determine the exact concentration level of $H_2O$ gas, if present. Signal channel detector output, $V_S$, associated with a path length $L_S$, 11 (see FIG. 1) and Reference channel detector output, $V_R$, associated with a path length $L_R$, 12 (see FIG. 1) are both functions of $H_2O$ gas concentration in sample chamber 5 (common to both $L_S$ and $L_R$) according to the well-known Beer-Lambert Law. Since by design $L_S > L_R$, the Beer-Lambert Law stipulates that $V_R$ is always greater than $V_S$. Furthermore, when there is no $H_2O$ gas in sample chamber 5, both $V_S$ and $V_R$ take on their maximum values.

Figure 2:
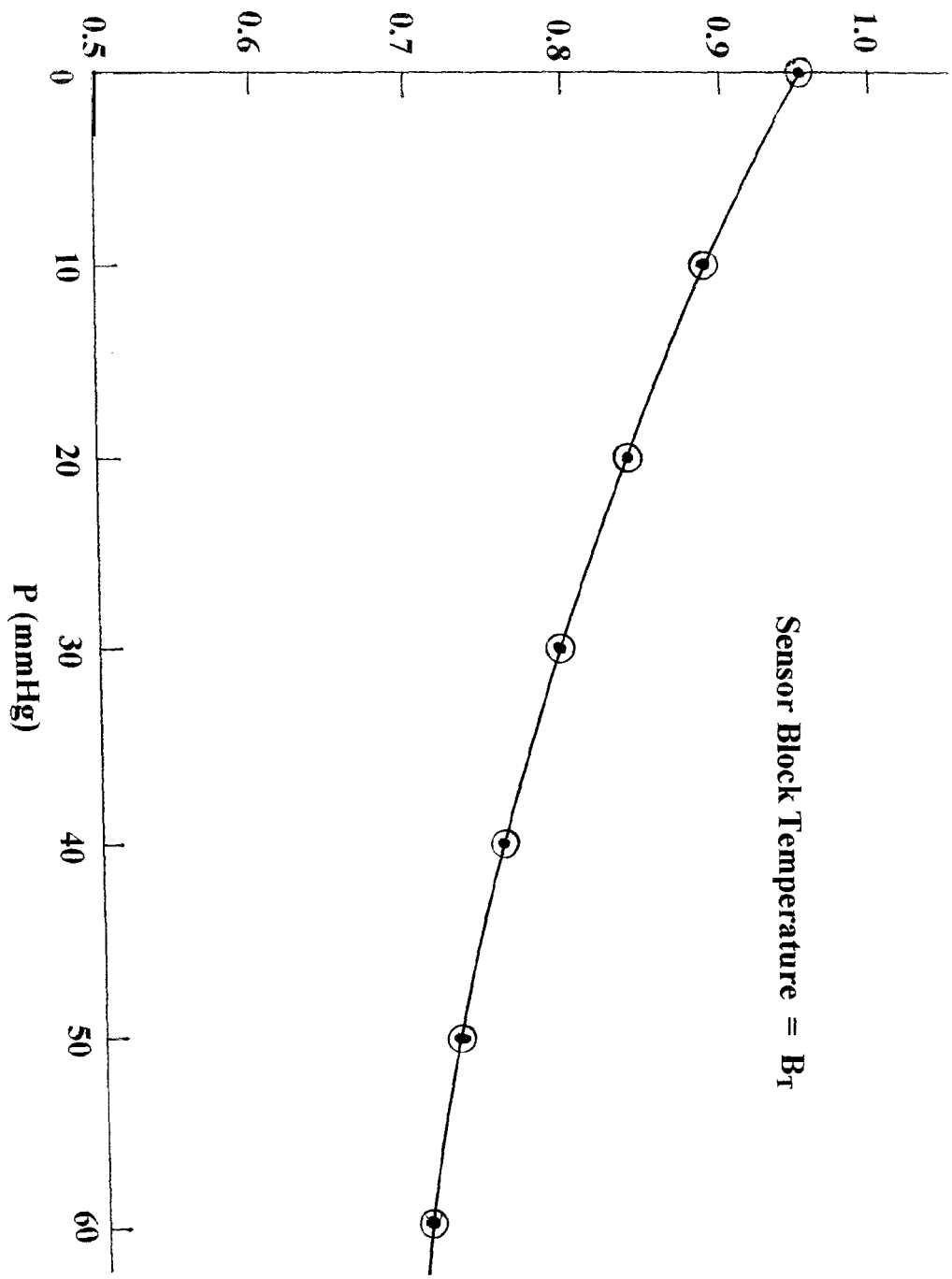
FIG. 2 is a data plot showing the values of $G(B_T)$ versus the concentration level of $H_2O$ in the sample chamber of the sensor.

The invariant Physics domain of the current invention is represented by the ratio $G(B_T) = V_S(B_T)/V_R(B_T)$ where $B_T$ is the temperature of the common thermal platform. The invariant Physics domain of the calibration curve for the sensor is established by plotting the values of $G(B_T)$ against various concentration levels of $H_2O$ in sample chamber 5. FIG. 2 shows such a plot at temperature $B_T$. Note that the value of $G(B_T)$ depends on $B_T$, which is linked to the ambient temperature wherein the sensor is located. Other than that, $G(B_T)$ is invariant since the Physics of gas measurement cannot change and both the Signal and Reference channels have similar detectors with identical spectral filters and sharing the same thermal platform at $B_T$ (see FIG. 1). $G(B_T)$ will not change even as the infrared source of the sensor ages with changes in its spectral output.

The variant sensor components characteristics domain is represented by a single parameter $G_0(B_T)$ which is the value of the ratio $V_S(B_T)/V_R(B_T)$ when there is no $H_2O$ present in the sample chamber 5. Note that $G(B_T)$ is not invariant in this domain. For example, if there is a radiation pattern change in the source due to aging and it does not affect the intensity of its spectral output, the different physical locations for the Signal channel and the Reference detectors will cause $G(B_T)$ to change. If the responsivity of the Signal channel detector changes differently over time from that of the Reference channel detector, $G(B_T)$ will also change. Like $G(B_T)$, $G_0(B_T)$ is still a function of $B_T$ but it is independent of the Physics of the gas measurement and it will change if the sensor components characteristics change.

The formulation of the calibration curve for the NDIR $H_2O$ or dew point sensor is achieved by combining together representations of the two domains described above. This is done by first normalizing $G(B_T)$ with $G_0(B_T)$ to form:

$$x = G(B_T)/G_0(B_T) \quad (1)$$

and then plotting the $H_2O$ concentration expressed as water vapor pressure (mmHg) or P(mmHg) in the sample chamber 5 (see FIG. 1) as a function of x as follows:

$$P(mmHg) = PX(x) = PX[G(B_T)/G_0(B_T)] \quad (2)$$

where PX is a function of x as given by Equation (1) above. Note that x is independent of $B_T$ or the ambient temperature wherein the NDIR $H_2O$ or dew point sensor is located as long as the representations $G(B_T)$ and $G_0(B_T)$ respectively for the invariant Physics domain and the variant sensor components characteristics domain are derived at the same $B_T$ temperature.

Conversely from Equation (2), one can express x as a function of P(mmHg) by $$x = XP[P(mmHg)] \quad (3)$$

so that one can determine the value of x when there is P(mmHg) of $H_2O$ present in the sample chamber of the sensor.

Finally, knowing that the value of $G_0(B_T)$ can only be obtained under a special situation, namely when there is no $H_2O$ gas present in the sample chamber of the sensor, its value cannot be determined when the sensor is making a gas measurement with gas present in the sample chamber. Therefore, to complete the calibration curve formulation, one has to obtain the value of $G_0(B_T)$ as a function of $B_T$ expressed by a function Q as $$G_0(B_T) = Q(B_T) \quad (4)$$

Equations (2) and (4) are now the calibration curves for the sensor. To use the sensor to make a $H_2O$ gas measurement, one first notes the sensor block temperature or $B_T$. Since $B_T$ is linked to the ambient temperature wherein the sensor is located, such a gas measurement does automatically take the ambient temperature into consideration. One then measures the value for $G(B_T)$ which is the ratio of the signal channel detector output over the Reference channel detector output at temperature $B_T$. Using Equation (4) above, one calculates the value for $G_0(B_T)$ at $B_T$ and combining that with $G(B_T)$ obtained earlier one gets the value of $x = G(B_T)/G_0(B_T)$. By plugging in the value of x into PX (x) of Equation (2), one obtains the $H_2O$ gas concentration P (mmHg).

Figure 3:
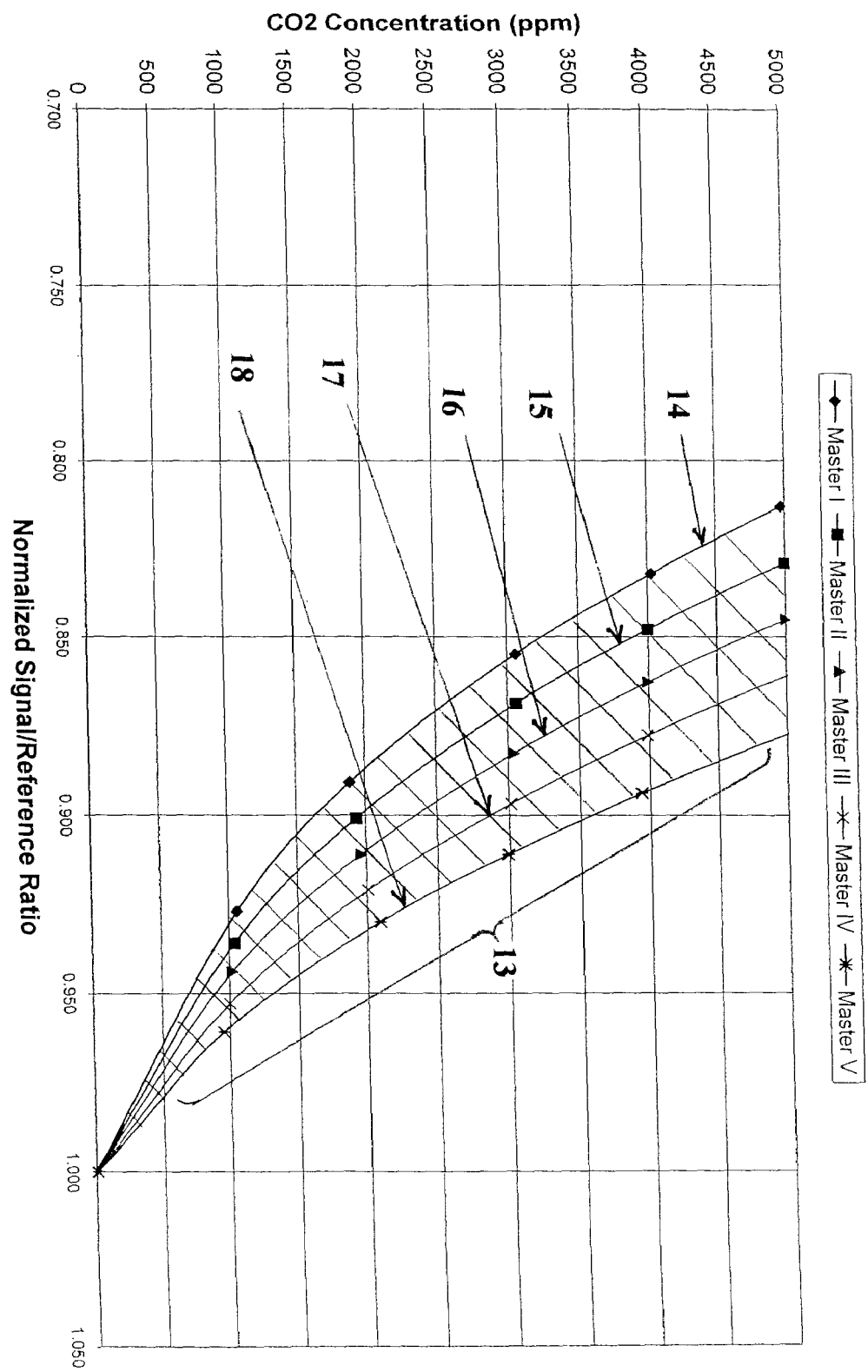
FIG. 3 is a data plot showing five Master Calibration curves used in accordance with the present invention to represent the band of calibration curves prepared for the sensors to be individually calibrated without the use of standard $H_2O$ gases.

So far we are able to explain how the current invention enables one to formulate the calibration curve for an NDIR $H_2O$ or dew point sensor into two distinct domains, one being the invariant Physics measurement domain and the other the variant sensor components characteristics domain. In order to obtain Equation (2) above, one still needs to prepare a number of $H_2O$ concentration level standards. But it is the subsequent elimination of this difficult and expensive experimental step needed for calibrating each and every NDIR $H_2O$ or dew point sensor that is the objective of the current invention. The current invention takes full advantage of the fact that because of the existence of the invariant Physics measurement domain for the calibration of the sensor, one needs only to deal with the variant sensor components characteristics domain. In principle, the invariant Physics measurement portion of the sensor's calibration should be the same for every $H_2O$ or dew sensor. However, during production of the sensors, the components for the sensors, especially the infrared source and the two infrared detectors with spectral filters, are similar but not identical. Consequently, even the invariant Physics measurement portion of the calibration curve for the sensors will vary slightly from one another. This is illustrated in FIG. 3. Shown in FIG. 3 are a large number of calibration curves for the $H_2O$ or dew point sensors (up to 64 units or more) at a particular temperature $B_T$ as a band 13. This band of calibration curves for the sensors is also represented by five specific curves, 14-18, equally spaced and covering all of the curves within the band. These five curves are called the Master Calibration curves for the sensors and the exact number of them is not critical and can vary from three to seven, for example, as long as the calibrating performance characteristics among all of sensors are represented. Note that the calibration curves shown in FIG. 3 place no restrictions at all to the $G_0(B_T)$ value for the individual sensors which represents the variant component characteristics domain for the sensors and is independent of the invariant Physics measurement domain. The number of NDIR gas sensors used to create calibration curves which are themselves used to create the Master Calibration curves should be sufficient to take into account a large enough range of performance differences in the components of the NDIR gas sensors in production so that they will meet specified accuracy requirements.

During production of the $H_2O$ or dew point sensors, the components going into each sensor cannot be individually characterized due to the constraint of their unit production cost. However, the range of their individual performance characteristics among all the produced sensors after assembly using non-identical components will be very adequately represented or covered by the band of calibration curves as shown in FIG. 3. In other words, the calibration curve for a particular sensor produced will be adequately represented by one of those in the band as shown in FIG. 3. The question now is how to develop an algorithm that will enable a particular produced sensor to correctly associate itself with one of the Master calibration curves representing the totality of the calibration curve band.

The calibration methodology of the current invention for a particular $H_2O$ or dew point sensor does not require use of $H_2O$ gas standards and instead uses a novel technique that will now be described. The first step of this technique is to install the five Master calibrating curves and the function $Q(B_T)$ [see Equation (4) above] into the CPU (or memory accessible by the CPU) of the just produced sensor to be calibrated. In principle, $G_0(B_T)$ is independent of $B_T$. However, characteristics variation of components constituting a particular sensor makes the latter slightly dependent on $B_T$. Although determining of the function $Q(B_T)$ is relatively straightforward and does not require gas standards, it is generally accurate enough to take $G_0(B_T)=G_0$, namely a constant independent of $B_T$. Thus for every sensor ready to be calibrated, the first step is to have the five Master calibration curves and its unique value of $G_0$ stored in its CPU (or memory accessible by its CPU).

The next step is to use any gas standard of no particular concentration level for calibrating the sensor. For example, the gas concentration of the space wherein the to-be-calibrated sensor is located can be used as the gas standard for calibration. By accurately determining the gas concentration level in such space using an accurate gas sensor called a Calibration Master, and then transmitting that gas concentration level information to the to-be-calibrated sensor (e.g., by using any appropriate wireless communication method or, less preferably, through a wire connection), the calibration job can be completed so long as the to-be-calibrated gas sensor is turned ON before the calibration starts.

Before the calibration routine is started, the to-be-calibrated gas sensor is turned ON and is making measurements. In particular, it is measuring the value of the ratio $V_S/V_R$ or G at $B_T$ all the time. When it receives the information for the correct gas concentration level in its locale (also at $B_T$) or P(mmHg), for each of the five Master Calibration curves stored, it uses the stored Equation (3), namely $$x = XP[P(mmHg)] \quad (3)$$

to calculate $x_i=XP_i[P(mmHg)]=G_i(B_T)/G_{0i}(B_T)$ where $i=1, 2, 3, 4$ and 5 respectively from each of the five Master Calibration curves stored. Since for every Master Calibration curve, $G_i(B_T)$ is invariant, the to-be-calibrated sensor can therefore calculate the values of $G_{0i}(B_T)$ by using its own measured G, namely, $$G_{0i}(B_T)=G/x_i; \quad i=1 \text{ to } 5$$

Now in order to pick the best Master Calibration curve for the to-be-calibrated sensor, the one with the minimum $|G_{0i}(B_T)-G_0|$ will be the best choice (or, if two curves have the same minimum, either such curve can be picked). The reason is the to-be-calibrated sensor is merely picking the invariant Physics measurement portion of the calibration curve that best matches its variant sensor components characteristics portion represented by $G_0$. Therefore, the curve that is associated with the closest $G_0$ value, namely the minimum value of $|G_{0i}(B_T)-G_0|$, will be the calibration curve for the sensor, namely the ith Master Calibration curve with $G_0=G_{0i}$.

It must be pointed out that the above described calibration methodology requires a couple of prerequisites in order for it to work properly. The first and most important one is the preparation of a family of calibration curves (the more the better, within reason taking into account changes between the number of such curves and computational time limits) for the sensor once their design and components have been firmly decided. This set of calibration curves will be used to determine the set of Master Calibration curves to be stored in every subsequent sensor produced. It is implicitly assumed that once this sensor is designed, it will not change in any way in the future that will change its invariant Physics domain otherwise another set of calibration curves for the sensor must then be prepared anew in order for this method to work again. But to generate this set of calibration curves in the beginning will require the use of expensive and difficult-to-prepare $H_2O$ gas standards. However, once they are prepared, this calibration methodology will work indefinitely for as long as the sensor design is not altered. For NDIR $H_2O$ or dew point sensors, an expensive two-pressure reactor discussed earlier can be used to generate these calibration curves. Although the instrument is expensive, the procedure to use it to generate the curves needed for calibration according to the present invention is rather simple and straightforward. Furthermore, this two-pressure reactor can also be used to verify the accuracy of sensors calibrated with the method invented here.

The second prerequisite is to program the proper temperature dependence of the $G_0$ value into the to-be calibrated sensors. As mentioned earlier, in principle the $G_0$ should be to a large extent temperature independent. However, the components for the manufacture of these sensors, though similar, are not identical. Consequently, a small temperature dependence of $G_0$ for the to-be-calibrated sensors is to be expected and must be adequately dealt with in order that the calibration will be accurate. Fortunately, no expensive and difficult-to-prepare $H_2O$ gas standards, but only 100% dry Nitrogen, is needed to deal with this problem. If nothing else, it is just time consuming.

Finally it is worth pointing out the fact that the currently invented calibration methodology is not only good for calibrating sensors for the first time without the need to use expensive and difficult-to-prepare $H_2O$ gas standards, it is also good for subsequent re-calibration of these sensors if they are found in time to be inaccurate. This extra advantage of the current methodology further adds credence to the upcoming low cost NDIR $H_2O$ or dew points sensors made possible because of it.

Thus, in summary, the present invention discloses a novel calibration method for a specially designed NDIR Absorption Biased $H_2O$ or Dew Point gas sensor that does not require difficult-to-prepare specified $H_2O$ gas standards. This methodology first divides up the sensor's calibration curve into two distinct portions. The first is the invariant NDIR Physics measurement portion represented by a polynomial F(G) linking the $H_2O$ concentration level in the sensor sample chamber, P(mmHg), to a parameter G which is the ratio of the Signal channel detector output to that of the Reference channel output. The second is the variant sensor components characteristics portion represented by a single parameter $G_0$ which is the same ratio G as before when there is no $H_2O$ present in the sample chamber. The calibration curves of a relatively large number of manufactured sensors, respectively represented individually by $P(mmHg)=F(G/G_0)$, are first obtained. Due to the fact that the components of these sensors are not identical, though similar, these calibration curves will be bunched together shaping like a fan. A number of equally spaced Master Calibration curves, typically three or more depending upon accuracy requirement, are devised to represent the entire family of these curves. These Master Calibration curves, similar in form to the individual ones, and their inverse function, namely $G/G_0=F^{-1}[P(mmHg)]$, are stored in the CPU of each to-be-calibrated sensor along with its own $G_0$. Any $H_2O$ gas concentration level can now be used to calibrate the sensor by first transmitting to it the correct $H_2O$ P(mmHg) in its sample chamber. The sensor uses the inverse function $F^{-1}[P(mmHg)]$ to first calculate the value of $G/G_0$ for each of the Master Calibration curves stored. Combining these values of $G/G_0$ with its own measured G value for the $H_2O$ concentration level in its sample chamber, the value of the correct $G_o$ for each Master Calibration curve can be determined. The Master Calibration curve that yields the closest $G_0$ value to that stored in the sensor will be selected as its calibration curve along with the new $G_0$ value.

While the invention has been described herein with reference to certain examples, those examples have been presented for illustration and explanation only, and not to limit the scope of the invention. Additional modifications and examples thereof will be obvious to those skilled in the art having the benefit of this detailed description. Further modifications are also possible in alternative embodiments without departing from the inventive concept.

Accordingly, it will be apparent to those skilled in the art that still further changes and modifications in the actual concepts described herein can readily be made without departing from the spirit and scope of the disclosed inventions as defined by the following claims.

What is claimed is:

1. A method for calibrating a dual-beam non-dispersive infrared ("NDIR") gas sensor having a sample chamber useful to detect a water vapor gas, comprising:
obtaining a variant sensor components domain ("$G_0$") of the NDIR gas sensor when there is no water vapor gas in the sample chamber;
obtaining a physics measurement domain ("G") of the NDIR gas sensor for a set of known concentrations of the water vapor gas in the sample chamber, the known concentrations being measurable quantities exceeding zero;
using G to calculate a $G_{0i}$ from a known concentration of water vapor in the sample chamber for each of a plurality of master calibration curves; and
selecting one of the plurality of master calibration curves as a calibration curve for the NDIR gas sensor by choosing one of the plurality of master calibration curves with a lowest difference between its $G_{0i}$ and the $G_0$ of the NDIR gas sensor as the calibration curve of the NDIR gas sensor.

2. The method of claim 1 wherein G and the $G_{0i}$ for each of a plurality of master calibration curves are obtained at substantially the same temperature.

3. The method of claim 1 wherein G is a signal channel output ("$V_S$") divided by a reference channel output ("$V_R$").

4. The method of claim 3 wherein the plurality of master calibration curves are obtained from a plurality of calibration curves obtained from a plurality of NDIR gas sensors, each of said plurality of calibration curves being represented by an equation of $P=F(G/G_0)$ where P is equal to a gas pressure and F is a function, and each of the plurality of NDIR gas sensors has an invariant physics measurement domain of its calibration curve which is similar to that of the physics measurement domain of the NDIR gas sensor.

5. The method of claim 4 wherein the plurality of master calibration curves are equally spaced.

6. The method of claim 5 wherein there is an odd number of curves in the plurality of master calibration curves.

7. The method of claim 6 wherein the odd number of curves is five and the plurality of NDIR gas sensors comprises at least fifty NDIR gas sensors.

8. The method of claim 4 wherein the plurality of master calibration curves represent the plurality of calibration curves.

9. The method of claim 4 wherein the plurality of master calibration curves represent a range of individual calibrating performance characteristics among the plurality of NDIR gas sensors.

10. A method for calibrating a dual-beam non-dispersive infrared ("NDIR") gas sensor useful to detect a water vapor gas, comprising:
obtaining a variant sensor components domain ("$G_0$") of the NDIR gas sensor when there is no water vapor gas in the sample chamber;
obtaining a physics measurement domain ("G") of the NDIR gas sensor for a set of known concentrations of the water vapor gas in the sample chamber, the known concentrations being measurable quantities exceeding zero;
using G to calculate a $G_{0i}$ from a known concentration of water vapor in the sample chamber for each of a plurality of master calibration curves; and
selecting one of the plurality of master calibration curves as a calibration curve for the NDIR gas sensor by choosing one of the plurality of master calibration curves with a lowest difference between its $G_{0i}$ and the $G_0$ of the NDIR gas sensor as the calibration curve of the NDIR gas sensor;
wherein G and the $G_{0i}$ for each of a plurality of master calibration curves are obtained at substantially the same temperature;
wherein G is a signal channel output ("$V_S$") divided by a reference channel output ("$V_R$");
wherein the plurality of master calibration curves are obtained from a plurality of calibration curves obtained from a plurality of NDIR gas sensors, each of said plurality of calibration curves being represented by an equation of $P=F(G/G_0)$ where P is equal to a gas pressure and F is a function, and each of the plurality of NDIR gas sensors has an invariant physics measurement domain of its calibration which is similar to that of the physics measurement component domain of the NDIR gas sensor; and
wherein the NDIR gas sensor and the plurality of NDIR gas sensors are comprised of:
an infrared source;
a reference detector that produces a reference output;
a signal detector that produces a signal output;
a sample chamber having a signal channel path length greater than a reference channel path length; and
electronics for determining a sample concentration of the water vapor gas;
wherein each of the reference detector and the signal detector have an identical narrow band pass filter with the same Center Wavelength ("CWL"), Full Width Half Maximum (FWHM) and transmittance efficiency at the CWL.

11. The method of claim 10 wherein the plurality of master calibration curves are equally spaced.

12. The dual-beam NDIR gas sensor of claim 11 further comprising means for receiving information transmission of a known concentration of water vapor in the sample chamber.

* * * * *